(12) United States Patent
Binder et al.

(10) Patent No.: US 10,308,582 B2
(45) Date of Patent: *Jun. 4, 2019

(54) PROCESS FOR MAKING ACRYLIC ACID FROM DEXTROSE

(71) Applicant: Archer Daniels Midland Company, Decatur, IL (US)

(72) Inventors: Thomas Binder, Marion, IA (US); Ahmad K. Hilaly, Forsyth, IL (US); Naveen S. Sudharsan, Malden, MA (US); Kris N. Mani, Basking Ridge, NJ (US); Mitchell Schultz, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 245 days.

This patent is subject to a terminal disclaimer.

(21) Appl. No.: 15/532,397

(22) PCT Filed: Nov. 23, 2015

(86) PCT No.: PCT/US2015/062087
§ 371 (c)(1),
(2) Date: Jun. 1, 2017

(87) PCT Pub. No.: WO2016/089644
PCT Pub. Date: Jun. 9, 2016

(65) Prior Publication Data
US 2017/0362156 A1   Dec. 21, 2017

Related U.S. Application Data

(60) Provisional application No. 62/086,331, filed on Dec. 2, 2014.

(51) Int. Cl.
| | | |
|---|---|---|
| C07C 51/377 | (2006.01) |
| C07C 51/02 | (2006.01) |
| C07C 51/43 | (2006.01) |
| C07C 51/42 | (2006.01) |
| C07C 51/44 | (2006.01) |
| C07C 51/47 | (2006.01) |
| C07C 51/48 | (2006.01) |
| C07C 57/04 | (2006.01) |
| C07C 57/065 | (2006.01) |
| C12P 7/56 | (2006.01) |
| B01D 3/14 | (2006.01) |
| B01D 3/02 | (2006.01) |
| B01D 11/04 | (2006.01) |
| B01D 61/14 | (2006.01) |
| B01J 43/00 | (2006.01) |
| C12P 7/40 | (2006.01) |
| B01D 15/18 | (2006.01) |
| B01D 15/36 | (2006.01) |
| B01D 61/02 | (2006.01) |
| C07C 51/41 | (2006.01) |

(52) U.S. Cl.
CPC ............. *C07C 51/377* (2013.01); *B01D 3/02* (2013.01); *B01D 3/145* (2013.01); *B01D 11/04* (2013.01); *B01D 15/1821* (2013.01); *B01D 15/364* (2013.01); *B01D 61/027* (2013.01); *B01J 43/00* (2013.01); *C07C 51/02* (2013.01); *C07C 51/412* (2013.01); *C07C 51/43* (2013.01); *C07C 51/44* (2013.01); *C07C 51/47* (2013.01); *C07C 57/04* (2013.01); *C12P 7/40* (2013.01); *C12P 7/56* (2013.01); *C12Y 101/01027* (2013.01); *B01D 2325/36* (2013.01)

(58) Field of Classification Search
None
See application file for complete search history.

(56) References Cited

U.S. PATENT DOCUMENTS

| | | | | |
|---|---|---|---|---|
| 4,698,303 A * | 10/1987 | Bailey | .................. | A23C 21/023 426/43 |
| 5,036,005 A * | 7/1991 | Tedder | ..................... | B01D 3/40 435/155 |
| 2013/0157328 A1* | 6/2013 | Ozmeral | ................. | C07C 67/08 435/135 |

FOREIGN PATENT DOCUMENTS

JP   2014189510 A   * 10/2014

* cited by examiner

*Primary Examiner* — Robert J Yamasaki
*Assistant Examiner* — Charles Zoltan Constantine
(74) *Attorney, Agent, or Firm* — William B. Miller

(57) ABSTRACT

A process is described for making acrylic acid from dextrose, which comprises fermenting dextrose; removing solids from the resulting fermentation broth; removing lactic acid from the clarified broth by extraction into an organic solvent; separating out the lactic acid-loaded organic solvent while recycling at least a portion of the remainder back to the fermentation step; reacting the lactic acid with ammonia to provide a dehydration feed comprising ammonium lactate while preferably recycling the organic solvent; carrying out a vapor phase dehydration of the ammonium lactate to produce a crude acrylic acid product; and purifying the crude acrylic acid by distillation followed by melt crystallization, chromatography or both melt crystallization and chromatography.

10 Claims, 6 Drawing Sheets

PROCESS FOR MAKING ACRYLIC ACID FROM DEXTROSE

CROSS-REFERENCE TO RELATED APPLICATION(S)

This application is a national stage entry of International Application No. PCT/US2015/062087, filed Nov. 23, 2015, which itself claims the benefit of U.S. Provisional Patent Application No. 62/086,331, filed Dec. 2, 2014, the contents of which are incorporated by this reference.

TECHNICAL FIELD

The present invention relates generally to processes for making biobased acrylic acid, and more particularly, to processes for making biobased acrylic acid from sugars.

BACKGROUND OF THE INVENTION

Acrylic acid is a valuable industrial commodity and has a variety of uses. Polymers made from acrylic acid are used for the manufacture of adhesives, binders, coatings, paints, polishes and superabsorbent polymers, the latter in turn being used in disposable absorbent articles including diapers and hygienic products, for example.

Currently acrylic acid is made from petroleum source materials. For example, acrylic acid has long been prepared by the catalytic oxidation of propylene. In recent years, however, with an increasing awareness of the need to develop renewable source-based processes for the manufacture of acrylic acid and other conventional petrochemicals, significant amounts of research have been devoted to the identification and development of processes for making acrylic acid from renewable resources.

A number of references thus describe methods for converting glycerol to acrylic acid and/or acrylates, commonly using glycerol such as that produced in the making of biodiesel (fatty acid methyl esters) from plant oils, see, e.g., U.S. Pat. No. 7,396,962 to DuBois et al. and references cited therein.

Of more immediate relevance to the process of the present invention, a number of efforts have likewise been made to develop processes for making acrylic acid from carbohydrate and/or carbohydrate-derived feedstocks. One feedstock that can be derived from carbohydrates and that has been closely evaluated is 3-hydroxypropionic acid, or 3-HPA. U.S. Pat. No. 2,859,240 to Holmen (1958) indicates that the dehydration of 3-HPA is a "comparatively simple and economical process", but concludes that "the starting material is neither low in cost or readily available in quantity" (col. 1, lines 55-58) Essentially the same assessment is offered 45 years later, wherein in Kumar et al., "Recent advances in biological production of 3-hydroxypropionic acid", Biotechnology Advances, vol. 31, pp. 945-961 (2013), the authors conclude despite "significant progress" in the preceding decade toward "commercial production . . . in the near future" that "many important issues still remain and require more extensive investigations."

Another feedstock that can be derived from carbohydrates and that has been the subject of considerable research as well is lactic acid. In the same 1958 Holmen patent, for example, lactic acid is indicated as having been recognized for some time as preferable to 3-HPA as a prospective feedstock due to its ready availability (referencing a 1950 review of efforts to that time to develop processes for converting lactic acid and the lower alkyl esters of lactic acid to acrylic acid and the corresponding lower alkyl esters of acrylic acid). A commercially viable process yet remains elusive as well for the conversion of lactic acid to acrylic acid, as evidenced by a number of ongoing applications for patent that have recently been filed.

WO 2012/033845 to Ozmeral et al, WO 2012/156921 to Dongare et al. and WO 2013/155245 to Lingoes et al. are representative of these ongoing efforts to develop a commercially viable process for converting lactic acid (and/or lactate esters) to acrylic acid (and/or the corresponding acrylate esters), and each in turn reviews a fairly substantial body of additional published art detailing prior work toward the same objective.

In WO 2012/033845, a fermentation broth containing ammonium lactate is described as processed according to one of four pathways to produce acrylic acid esters. In a first pathway, lactic acid is first purified from the fermentation broth. The highly purified lactic acid is then subjected to a vapor phase dehydration reaction at elevated temperatures and in the presence of an appropriate catalyst to produce acrylic acid, which in turn is esterified in the presence of an esterification catalyst to provide the acrylate esters. In a second pathway, lactic acid in the fermentation broth is dehydrated "without much purification", followed by an esterification to produce acrylic acid esters. In the third pathway, ammonium lactate in the fermentation broth is subjected to simultaneous dehydration and esterification reactions to produce an acrylic acid ester product, while in the fourth pathway, ammonium lactate in the fermentation broth without much purification is subjected first to an esterification reaction to produce a lactic acid ester, and then this lactic acid ester is dehydrated to provide an acrylic acid ester product. In a "most preferred" embodiment according to this fourth pathway, a fermentation broth containing ammonium lactate is concentrated by evaporation of water and subjected to esterification with a C1-C10 alkyl alcohol, preferably in the absence of any exogenous esterification catalyst. Ammonia released during the concentration process is captured for recycling to the lactic acid fermentation, along with further ammonia released during the esterification reaction. The lactic acid ester obtained in the first stage is then dehydrated to produce a corresponding acrylic acid ester.

In WO 2012/156921 to Dongare et al., a catalyst with improved selectivity to acrylic acid from lactic acid and reduced production of acetaldehyde and other products is offered for use in the dehydration of lactic acid to acrylic acid, comprising a calcium phosphate in a calcium to phosphate ratio of from 1.5 to 1.9 as optionally modified with 5 weight percent of sodium. The process is described as involving preheating the catalyst in a fixed-bed reactor at a temperature of 370 to 380 degrees Celsius for from 20 to 40 minutes under highly pure nitrogen, then passing 50-80 wt. pct preheated vapors of a lactic acid solution through a quartz fixed catalyst bed reactor by means of a nitrogen carrier gas. Reported lactic acid conversion under these conditions was 100 percent, with 60 to 80 percent selectivity for acrylic acid and 15-35 percent selectivity for acetaldehyde.

In WO 2013/155245 to Lingoes et al., reference is made initially to research by a number of parties of a similar character to that reported in Dongare et al., which research confirmed that phosphate and nitrate salts may desirably change the surface acidity of acidic catalysts to inhibit the decarbonylation/decarboxylation of lactic acid to acetaldehyde in particular.

Lingoes et al. contend that even with a reduced selectivity to acetaldehyde, nevertheless even the reduced amounts are problematic, as byproducts can be deposited on the catalyst and result in fouling and in premature and rapid deactivation of the catalyst. Further, once deposited, the byproducts can catalyze other undesired reactions, for example, polymerization reactions (para. 0005).

As well, apart from the difficulties caused by being deposited on the catalyst in question, Lingoes et al. point out the difficulties even very small amounts of byproducts such as acetaldehyde, propanoic acid, carbon monoxide, carbon dioxide, 2-3-pentanedione and lactic acid oligomers can cause in processing acrylic acid from the then-known lactic to acrylic processes to make superabsorbent polymers, such that a significant body of literature existed around removal of these impurities from the acrylic acid.

Lingoes et al. reference U.S. Pat. No. 6,541,665 and U.S. Published Pat. Appl. 2011/0257355 as exemplars of this body of literature. In U.S. Pat. No. 6,541,665, a 5-stage crystallization (containing two purification stages and three stripping stages) was effective to obtain 99.94% acrylic acid containing 2600 parts per million by weight of acetic acid and 358 ppm of propanoic acid, among other species. In U.S. 2011/0257355, a method is described of removing propanoic acid in a single pass crystallization from a crude reaction mixture derived from glycerol dehydration/oxidation to obtain 99% acrylic acid. According to Lingoes et al, prior to their improved catalyst and process, the prior art methods for converting lactic acid to acrylic acid produced amounts of byproducts that were too high ("far too high") to even utilize such purification methods.

SUMMARY OF THE INVENTION

The present invention in one aspect concerns a process for making acrylic acid from dextrose, comprising:
a) fermenting dextrose in the presence of a biological catalyst to produce a fermentation broth containing lactic acid;
b) removing solids from the fermentation broth to produce a clarified fermentation broth;
c) removing lactic acid from the clarified fermentation broth by extraction into an organic solvent;
d) separating the lactic acid-loaded organic solvent from the fermentation broth remainder after lactic acid has been removed therefrom;
e) recycling at least a portion of the fermentation broth remainder to the fermentation step;
f) reacting lactic acid in the lactic acid-loaded solvent with ammonia to provide a crude dehydration feed comprising ammonium lactate;
g) separating ammonium lactate from organic solvent in the crude dehydration feed to provide a dehydration feed;
h) carrying out a vapor phase dehydration of ammonium lactate in the dehydration feed to produce a crude acrylic acid product;
i) purifying the crude acrylic acid product to provide a purified acrylic acid product, by a process including
a first distillation to remove acetaldehyde and ammonia overhead and provide a bottoms stream comprised predominantly of acrylic acid and propionic acid, and
a second distillation of the bottoms stream from the first distillation to provide a second distillation overhead stream enriched in acrylic acid and a second distillation bottoms stream enriched in propionic acid;
and,
j) further purifying the acrylic acid in the second distillation overhead stream by melt crystallization, chromatography or both melt crystallization and chromatography.

In one embodiment, the purified acrylic acid product is at least of an acceptable purity to be commercially sold as glacial acrylic acid.

In another embodiment, the purified acrylic acid product contains less than 3000 ppm by weight of propionic acid.

In another embodiment, the purified acrylic acid product contains less than 1000 ppm by weight of propionic acid.

In another embodiment of a process according to the present invention, the process further comprises carrying out an oxidative dehydrogenation of propionic acid in the second distillation bottoms stream in the presence of a suitable catalyst to provide additional acrylic acid. This additional acrylic acid may then be purified by melt crystallization, chromatography or both melt crystallization and chromatography, as appropriate given any unconverted propionic acid remaining and applicable propionic acid limits for achieving a desired glacial acrylic acid product (as purity requirements for both manufacturers and purchasers of glacial acrylic acid from conventional petroleum derived feedstocks do vary somewhat). Typically, though not necessarily, this will be done at least in part by recycling acrylic acid from the oxidative dehydrogenation of propionic acid in the second distillation bottoms stream for combining with the acrylic acid in the second distillation overhead stream prior to its purification by melt crystallization, chromatography or both melt crystallization and chromatography.

In another embodiment, the process further comprises carrying out an hydrogenation of acrylic acid in the second distillation bottoms stream with a source of hydrogen in the presence of a suitable catalyst to produce a commercial quality propionic acid co-product from the second distillation bottoms stream.

DESCRIPTION OF ILLUSTRATIVE EMBODIMENTS OF THE INVENTION

Figure 1A:
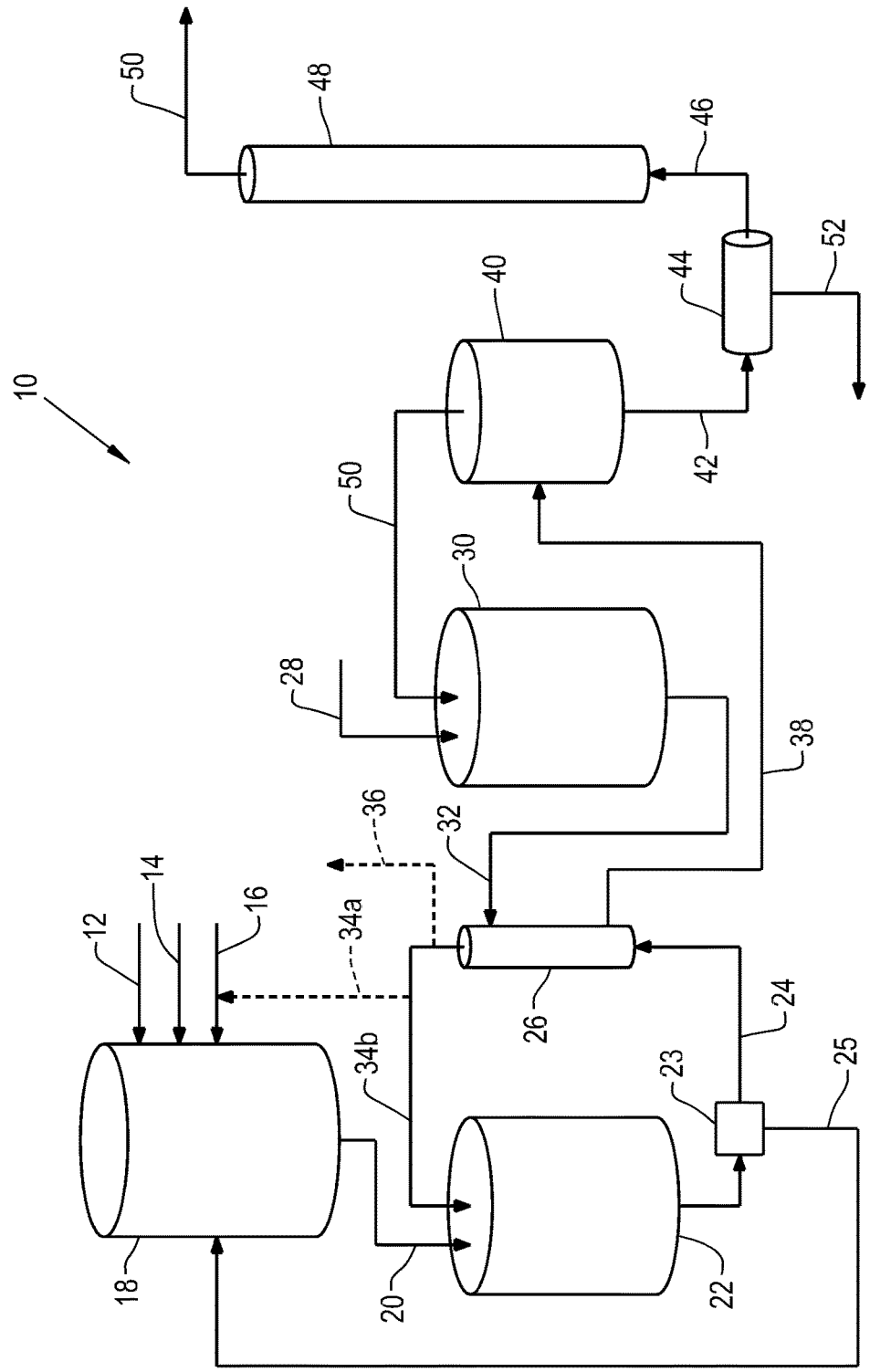
FIG. 1A is a schematic illustration of a portion of a process according to the present invention, in one embodiment.
Figure 1B:
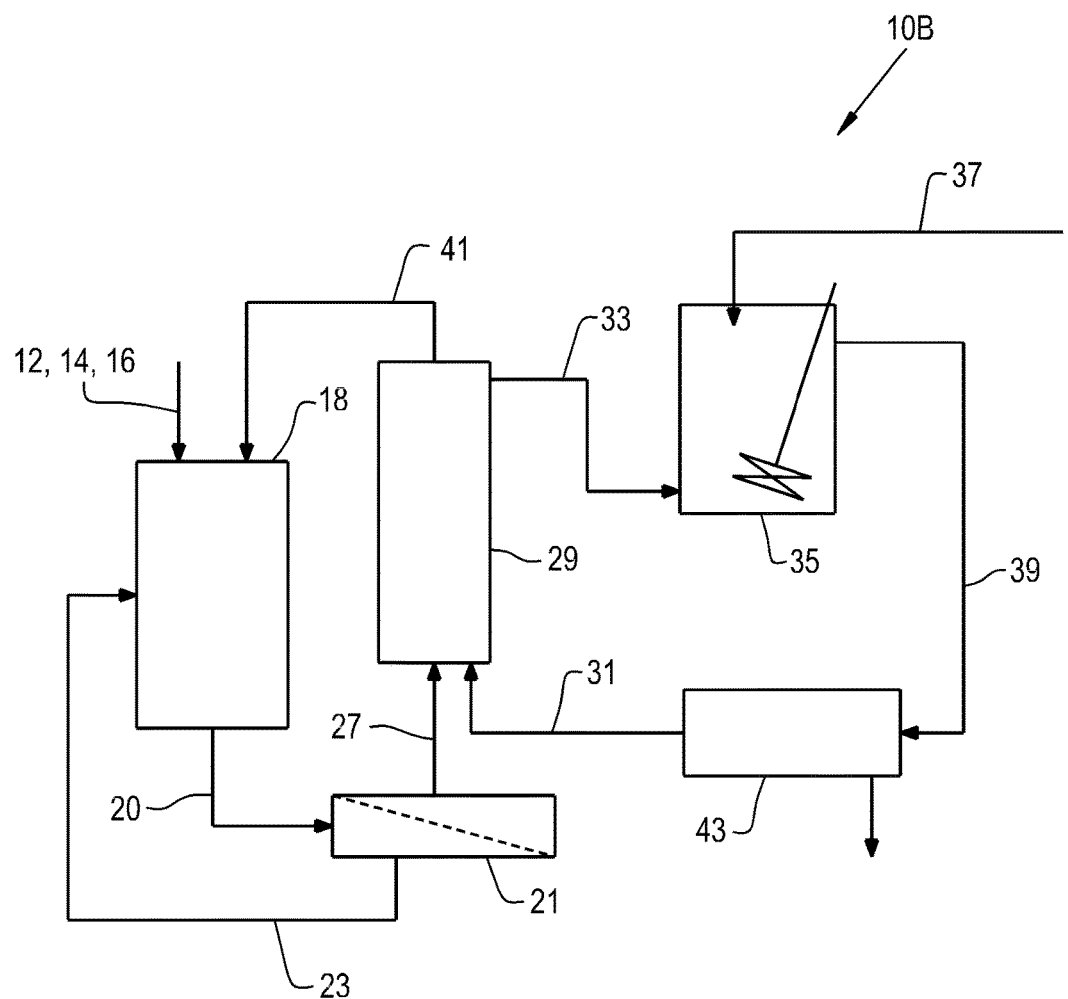
FIG. 1B is a schematic illustration of a portion of a process according to the present invention, in an alternative embodiment.
Figure 2:
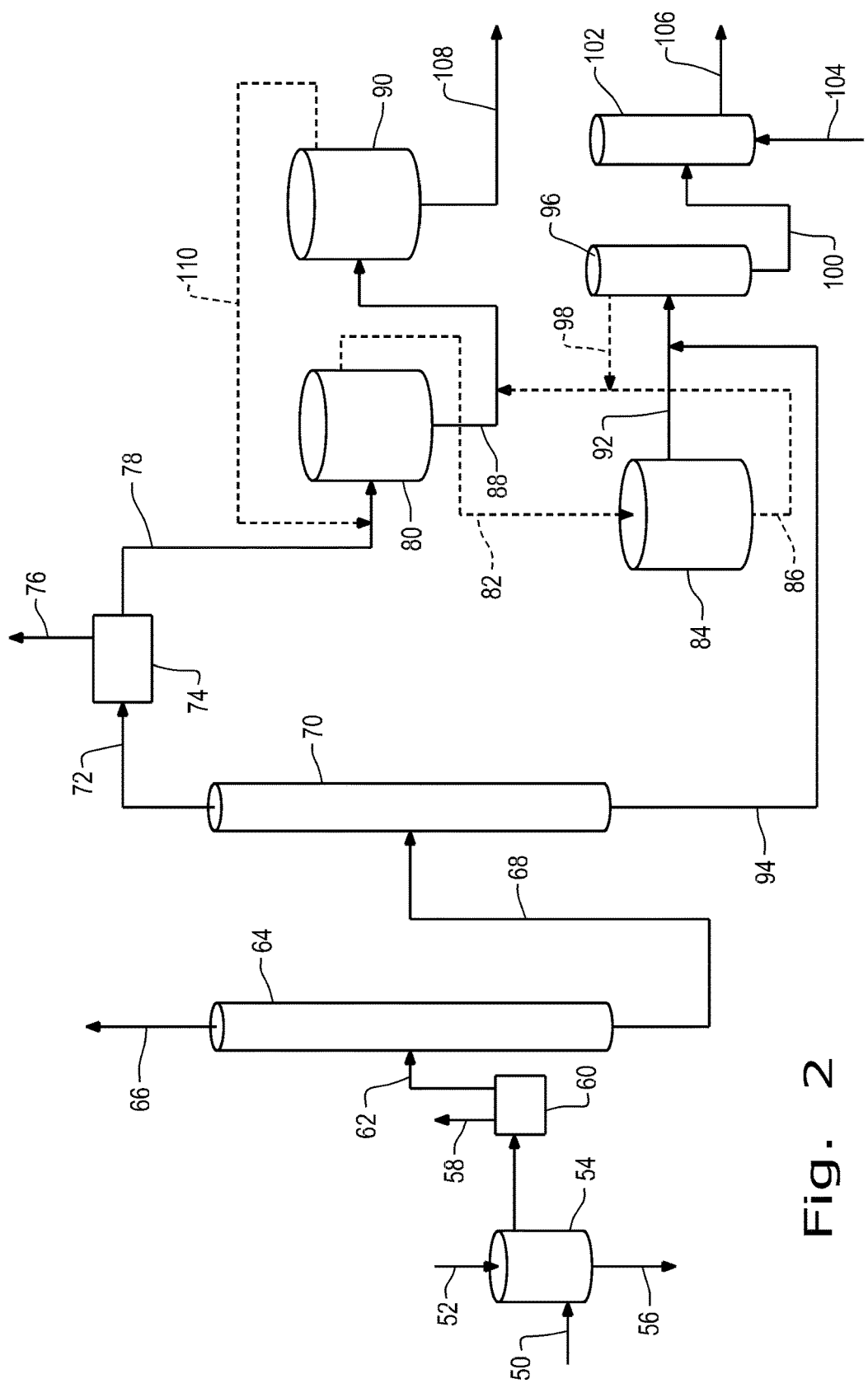
FIG. 2 is a schematic illustration of a second, downstream portion of a process according to the present invention, in one embodiment.

Turning now to FIGS. 1A/1B and FIG. 2, one illustrative embodiment of a process according to the present invention is shown schematically in two parts, with two possible configurations shown in FIGS. 1A and 1B for a first part of an overall process according to the present invention. FIGS. 1A and 1B depict alternative configurations for a first, upstream portion of a process for continuously generating a crude acrylic acid product stream, while FIG. 2 depicts a second, downstream portion directed to the purification of the crude acrylic acid product stream whereby a commercially acceptable, glacial acrylic acid product may be continuously produced.

Turning now to the upstream portion of a process as illustrated in one embodiment (10) in FIG. 1A, dextrose 12 is supplied with a microorganism 14 and with nutrients 16 for the microorganism 14 to a fermenter 18, wherein dextrose is biologically converted to lactic acid in the form of a lactic acid-containing fermentation broth 20.

The fermentation of dextrose to provide a lactic acid-containing fermentation broth is commercially-practiced, and those skilled in the art will be familiar with a number of microorganisms and related methods which could be employed for producing lactic acid from dextrose in the fermenter. Examples of suitable methods include those described in U.S. 2012/0214214 to Hara et al. (using an acid-resistant transformant of *Schizosaccharomyces pombe*), RU 2268304 C1 to Sineokij et al. (using a recombinant strain of *Schizosaccharomyces pombe*), and U.S. 2005/0112737 to Liu et al. (using an acid-tolerant yeast strain comprising a genome that includes an exogenous lactate dehydrogenase gene), all of which are hereby incorporated herein by reference.

Lactic acid-containing fermentation broth 20 is collected in the illustrated embodiment in a lactic broth tank 22. As is conventional in the art of processing of fermentation broths generally, a solids removal step 23 then removes solids from the lactic acid-containing fermentation broth 20 to provide a clarified lactic acid-containing fermentation broth 24 from which cell debris, for example, has been removed (as schematically indicated by reference number 25). Various means are well known in the art of processing fermentation broths for removing solids and could accordingly be employed in solids removal step 23, including but not being limited to various forms of filtration, flocculation, settling, centrifugation and the like, however in a preferred embodiment ultrafiltration is used.

The clarified fermentation broth 24 is in any event then continuously supplied to a solvent extraction step 26 for removing lactic acid from the fermentation broth 24 into a suitable organic solvent, while recovered cell bodies in 25 are recycled to the fermenter 18. In one embodiment, the solvent extraction step 26 involves the use of a plurality of hollow fiber membranes arranged in a shell-and-tube type configuration, though many different membrane configurations are known and may be selected for use. For example, a planar sheet membrane or stack of planar sheet membranes may be used, or a plurality of concentric tubular membranes arranged in a spiral configuration (commonly known as a spiral filter) may be used. Those skilled in the art and familiar with membrane-based gas recovery or separation systems will be well able to select the appropriate membrane system and configuration, but a presently preferred embodiment will employ hydrophilic nanofiltration membranes. As demonstrated in the examples below, the types of hydrophobic membranes employed in Liqui-Cel™ membrane contactors as sold by Membrana GmbH, Wuppertal, Germany, could also be used but are presently less preferred.

In an embodiment using hollow fiber membranes arranged in a shell-and-tube type configuration, an organic solvent to which ammonium hydroxide 28 has been added in solvent tank 30 is supplied via stream 32 to the shell side of the hollow fiber membranes employed for the step 26. Lactic acid from the aqueous lactic acid-containing feed 24 moves along and radially through the hollow fiber membranes to form ammonium lactate on the shell side in the solvent. The lactic acid-depleted remainder of the feed 24 can then preferably be recycled at least in part via stream 34a to utilize additional nutrients contained therein for supporting the fermentation in fermenter 18, with any of the lactic acid-depleted remainder not so used being recycled as shown via stream 34b to the lactic broth tank 22, but for a purge portion 36 as needed to maintain a desired lactic acid concentration in the lactic broth tank 22 and in the aqueous lactic acid-containing feed 24.

The ammonium lactate is meanwhile supplied in the solvent via stream 38 to a settling tank 40, wherein the ammonium lactate is concentrated by gravitational settling and partly separated from the organic solvent. In an optional added step, prior to settling tank 40, residual anionic species (for example, phosphorus, sulfur, aluminum and iron) and color bodies which may have been transferred to the organic solvent with the lactic acid may be removed by one or more of adsorption with adsorptive media and/or ion exchange or exclusion, according to known methods and using ordinary skill. Ammonium lactate solution 42 from the bottom of settling tank 40 then is communicated to a vaporizer 44 for supplying a vaporous ammonium lactate feed 46 to a dehydration reactor 48, while recovered solvent is recycled in stream 50 from the top of settling tank 40 for reuse. A small purge 52 is taken from the vaporizer 44 as indicated to maintain the ammonium lactate concentration in the vaporous ammonium lactate feed in a desired range.

In the reactor 48, ammonium lactate in the vaporous ammonium lactate feed 46 is dehydrated to products inclusive of acrylic acid and small amounts of other byproducts, such as, for example, propionic acid, acetaldehyde, carbon monoxide and carbon dioxide. A variety of dehydration catalysts and associated methods can be contemplated for use in the reactor 48, but in one embodiment, an aqueous inorganic base-treated aluminum phosphate catalyst such as described in U.S. Pat. No. 4,786,756 to Paparizos et al. is used, such patent now being incorporated by reference herein. In Paparizos et al., lactic acid and/or ammonium lactate is converted to acrylic acid in the vapor phase by contacting a mixture of water and lactic acid and/or ammonium lactate at from 0.1 to 50, usually 0.5 to 50, moles of steam per mole of lactic acid and/or ammonium lactate, with aluminum phosphate which has been treated with an aqueous inorganic base and calcined at a temperature in the range from 300 degrees to 650 degrees Celsius, usually 450 to 550 degrees Celsius, for from 10 minutes to 20 hours, typically 30 minutes to 10 hours. The reaction is carried out at a temperature of from 250 to 500 degrees Celsius, usually from 320 to 375 degrees Celsius, and at a contact time of 0.1 to 15, usually 2 to 4, seconds. Where ammonium lactate is dehydrated, lactic acid and ammonia are produced, and the ammonia can be used as a nutrient, if desired, in the fermentation of dextrose to lactic acid. In reference to FIG. 1, stream 34a can thus be recycled at least in part to the fermenter 18, with any ammonia not reacted with lactic acid in extractive membrane unit 26 and passing through the membrane into the aqueous lactic acid-containing fermentation broth 20 providing additional nutrients for the ongoing fermentation in the fermenter 18.

FIG. 1B depicts an alternative configuration for a first, upstream portion of a process for continuously generating a crude acrylic acid product stream. In one embodiment 10B, dextrose, a microorganism and nutrients for the microorganism 12, 14 and 16 are supplied as in FIG. 1A to a fermenter 18, wherein dextrose is biologically converted to lactic acid in the form of a lactic acid-containing fermentation broth 20.

The fermentation broth 20 undergoes ultrafiltration in an ultrafiltration step 21, generating a recycle stream 23 of cell bodies that are returned to the fermenter 18 and a clarified fermentation broth 27 that is supplied to a solvent extraction step 29. In solvent extraction step 29, an organic solvent 31 is either intimately mixed with the clarified fermentation broth 27 to extract lactic acid therefrom or more preferably a hydrophilic nanofiltration membrane material is used therein to allow lactic acid to be removed from the clarified fermentation broth into the organic solvent, while concurrently substantially preventing organic solvent from entering into the fermentation broth and higher molecular weight color bodies from the fermentation broth from entering into the organic solvent with the lactic acid. As before, various hydrophilic nanofiltration membrane materials can be used, in various known spatial configurations within the skill of the ordinary practitioner.

An organic solvent stream containing extracted lactic acid (33) then proceeds to a vessel 35 wherein ammonia supplied in an aqueous ammonium hydroxide stream 37 reacts with the extracted lactic acid to form an ammonium lactate product 39, while a fermentation broth remainder 41 from which lactic acid has been removed is recycled back to the fermenter 18.

The ammonium lactate product 39 is then phase separated in a vessel 43 to provide an aqueous ammonium lactate solution 45 that is then supplied, in the manner of stream 42 in the embodiment of FIG. 1A, to a vaporizer 44 for undergoing a vapor phase dehydration in reactor 48. The organic phase containing regenerated organic solvent is then recycled via stream 31 (with any additional makeup solvent as needed) for further use in recovering lactic acid from additional of the clarified fermentation broth 27.

Referring now to a second portion of an illustrative embodiment of a process of the present invention as schematically shown in FIG. 2, the dehydration accomplished in the reactor 48 produces a crude acrylic acid product 50 comprising acrylic acid, propionic acid, acetaldehyde, ammonia, carbon dioxide and carbon monoxide as well as a considerable quantity of water. Most of this water is separated out from the remainder of the crude acrylic acid product 50 by extracting organics from the crude acrylic acid product 50 into a suitable countercurrently flowing extractant 52, for example, ethyl acrylate, in an extraction column 54. Excess water is removed via stream 56, before lighter organic components (ammonia, carbon monoxide and carbon dioxide) are flashed off in stream 58 from a subsequent flash vessel 60 as shown in FIG. 2. The remainder, in the form of a first distillation column feed 62, is distilled in a first distillation column 64 to remove preferably substantially all of the residual, lighter components other than acrylic acid and propionic acid (e.g., ammonia, acetic acid, formic acid and acetaldehyde) overhead in stream 66, while the bottoms stream 68 comprised predominantly and preferably substantially entirely of acrylic acid and propionic acid is fed to a second distillation column 70 operating under very low pressures (for example, on the order of 10 kPa (0.1 bars)) for accomplishing preferably as complete a separation of the acrylic and propionic acids in the crude acrylic acid product 50 as can be achieved, by means of distillation alone.

Since the boiling points of acrylic acid and propionic acid are very close to one another, a second distillation overhead stream 72 containing most of the desired acrylic acid from crude acrylic acid product 50 is nevertheless passed in the illustrated embodiment to further purification means. In one embodiment, the further purification means will be as described in commonly-assigned WO 2015/031182 to Schultz et al., which is hereby incorporated herein by reference. Thus, in one embodiment (to which several of the examples below relate), chromatography, especially simulated moving bed chromatography, is used for separating out excess propionic acid from the second distillation overhead stream 72, preferably to an extent whereby a glacial acrylic acid-quality product results. In another embodiment, chromatography is employed in combination with crystallization for separating out excess propionic acid and providing a reduced propionic acid, biobased acrylic acid product that is preferably of a glacial acrylic acid purity.

Continuous industrial-scale adsorption processes are well known for their efficiency. The operation of a continuous countercurrent moving bed chromatographic apparatus in particular enhances the mass transfer driving force, allowing higher processed throughput for a given quantity of adsorbent and a more complete separation of desired components as compared to traditional batch elution chromatography. Nevertheless, in this countercurrent mode of operation both fluid and solid phases must be in motion. The movement of the solids presents considerable technical problems, however, including erosion of the adsorbent (causing fines leading to high pressure drops) and equipment abrasion. Because of these difficulties, simulated moving bed chromatographic systems have been developed wherein the solid adsorbent is kept static but a periodic one-column shift is performed of all inlet as outlet streams in the direction of the fluid flow. In this manner, an apparent or simulated countercurrent movement of the solid is created relative to the fluid flow. Such simulated moving bed chromatographic systems are widely used in a number of industries and for a variety of applications, and are the preferred approach wherein chromatography is used for removing excess propionic acid from, for example, the overhead stream 72 from the second distillation column 70, and providing a reduced propionic acid content acrylic acid product containing preferably less than 3000 ppm by weight of propionic acid, and more preferably less than 1000 ppm by weight of propionic acid.

A detailed treatment of simulated moving bed chromatographic systems, their design and operation need not be undertaken herein, as these systems are in use and well-known; nevertheless, those skilled in the art may find additional information as desired in the open literature, for example, in Gomes and Rodrigues, "Simulated Moving Bed Chromatography: From Concept to Proof-of-Concept", *Chemical Engineering Technology*, vol. 35, No. 1, pp 17-34 (2011) which article is hereby incorporated herein by reference, and will be guided by examples described below.

The just-referenced examples show that amphoteric resins—including both cationic and anionic functional groups attached to a polystyrene matrix—are effective chromatographic resins for our application. These resins are typically used for the separation of an electrolyte and non-electrolyte, or for the separation of two electrolytes. Various amphoteric chromatography resins are commercially available in addition to the DIAION AMP-03 amphoteric ion exchange resin sold by Mitsubishi Chemical and employed in several examples below, and may be used. For instance, an earlier version of the same resin was sold under the DIAION AMP-01 tradename and may be commercially available still to an extent; though reportedly of a different and perhaps less uniform bead size, this earlier version of the resin should also be suitable for use in the process step 16.

The DIAION AMP-03 amphoteric ion exchange resin itself is described by its supplier as an amphoteric ion exchange resin in which a quaternary ammonium group and a carboxy group are incorporated on a cross-linked polystyrene frame, having a uniform bead size of 260 μm and outstanding resistance to degradation and leaching. Suggested applications use water as the eluent (mobile phase) to separate various salts in an aqueous solution; accordingly it is expected that in an alternate embodiment, the propionic and acrylic acid in overhead stream 72 may be separated using the DIAION AMP-03 amphoteric ion exchange resin or a similar amphoteric resin by forming propionate and acrylate esters from the propionic and acrylic acids and then separating these esters.

Figure 3:
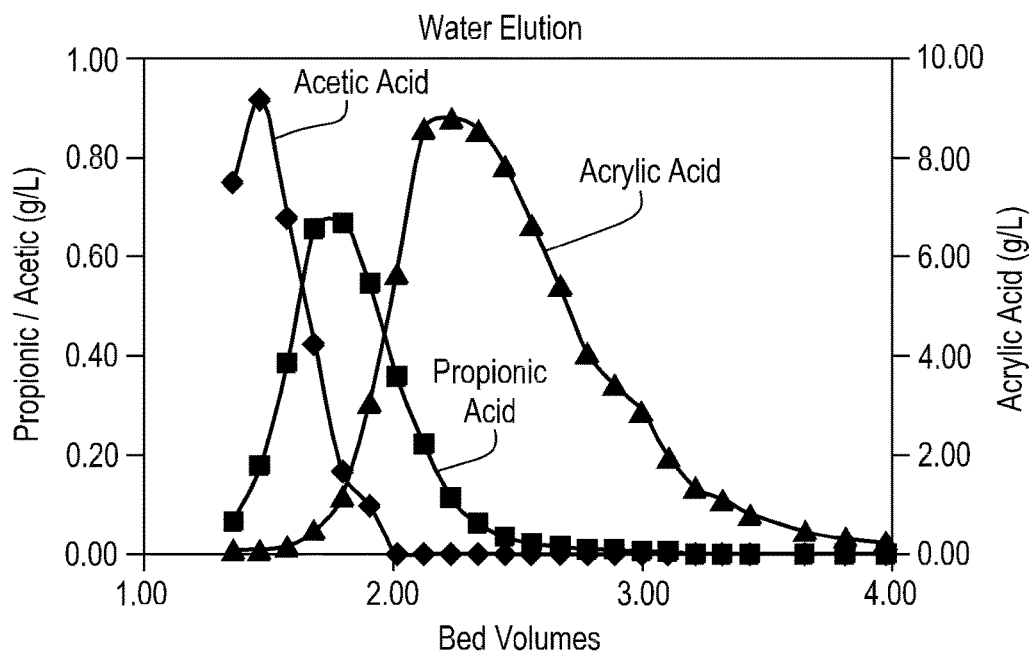
FIG. 3 depicts the results of pulse testing with an amphoteric resin for use in performing a chromatographic separation of excess propionic acid from an acrylic acid product in a process as schematically depicted in FIGS. 1 and 2, for example, using water as the eluent.
Figure 4:
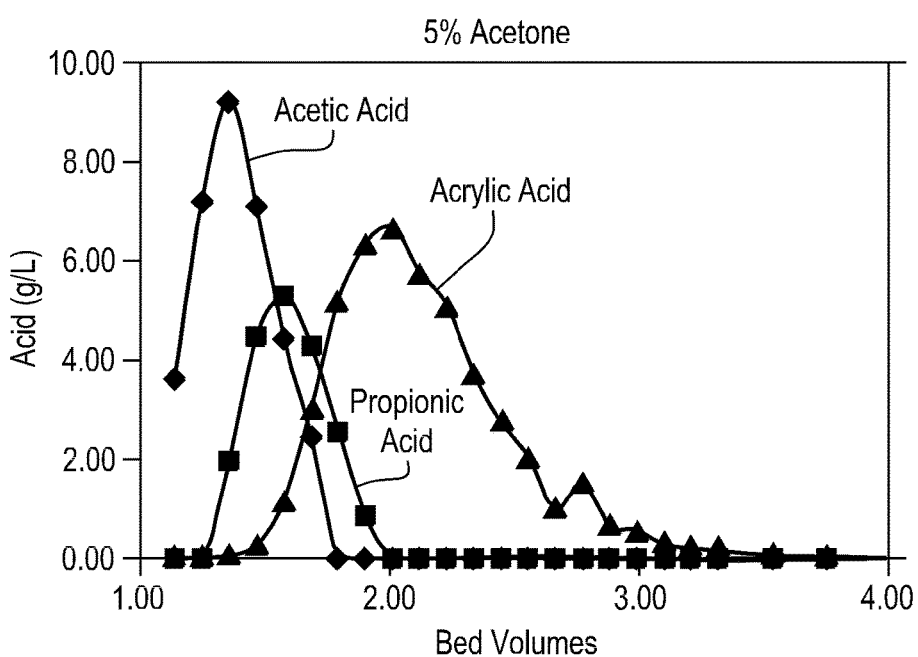
FIG. 4 depicts the results of pulse testing of the same resin system, but using a mixed eluent of 5% acetone in water.
Figure 5:
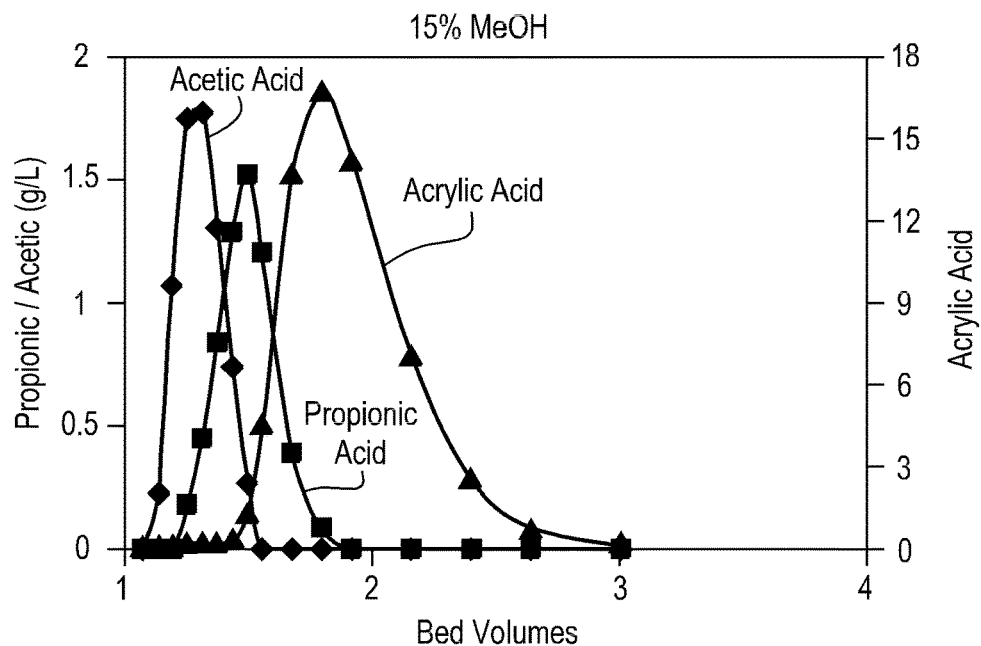
FIG. 5 depicts the results of pulse testing using a methanol co-solvent rather than acetone.
Figure 6:
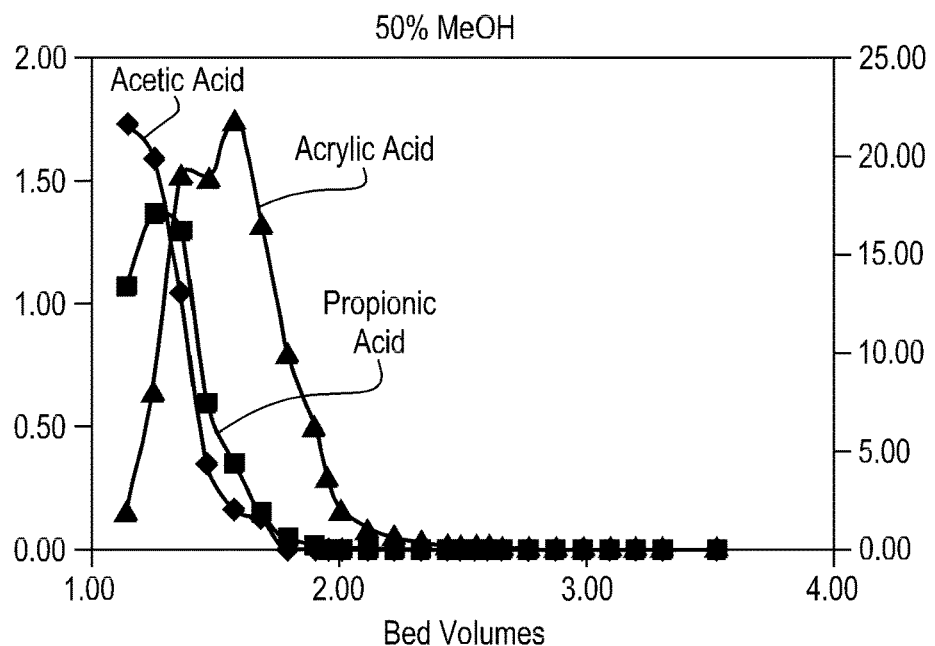
FIG. 6 depicts the results of pulse testing using a higher percentage of the methanol co-solvent.

Using water as the eluent (as suggested by Mitsubishi for the separation of salts) would likely require significant quantities of water, as shown by the pulse testing whose results are shown in FIG. 3, because of the retention time of acrylic acid and the slight tailing of the acrylic acid peak evident in FIG. 3. Preferably, then, the eluent is a combination of water with one or more organic solvents. Both methanol and acetone proved effective (as shown by FIGS. 4-6) in reducing the retention time of the acrylic acid peak and in reducing elution requirements overall, though those skilled in the art will be well able to identify other organic solvents that would accomplish these ends, and to optimize their use with water after the manner of the examples below.

Excess propionic acid may also be removed in other embodiments by a combination of chromatography and crystallization. The use of both melt and fractional crystallization for the purification of acrylic acid is very well-known and established, and various dynamic, suspension and static crystallization methods and devices are known. Melt crystallization fundamentally operates by isolating a compound from a melt by cooling and crystallizing the desired product according to the thermodynamic equilibrium of the initial system, and in the context of the present invention is used to produce an acrylic acid having a reduced propionic acid content compared to the solution of propionic acid-containing acrylic acid fed to a crystallizer, as well as a mother liquor retaining propionic acid in solution.

It is considered that any known crystallizer may be employed, and the type or size thereof is not particularly limited. Falling film crystallizers, for example, of the type sold by Sulzer Ltd., Winterthur, Switzerland, are a type of dynamic layer crystallization device presently used for purifying acrylic acid and may be used in one embodiment for the several melt crystallization stages depicted in the particular embodiment of FIG. 2, though U.S. Pat. No. 8,440,859 to Dubois expresses a preference for a series of falling film crystallizers followed by a final static crystallizer. In most falling film crystallizers, the purified acrylic acid crystallizes on the inside surface of a tube, though a falling film crystallizer is described in Le Page Mostefa et al., "A purification route of bio-acrylic acid by melt crystallization respectful of environmental constraints", Powder Technology, vol. 255, pp. 98-102 (2014) wherein the acrylic acid crystallizes on the external surface of a tube. According to the authors, such a configuration enables a larger portion of the initial melt to be crystallized without the risk of plugging that would occur if the crystallization were on the inside surface of a tube, and higher productivity can be obtained from the crystallizer. The authors also claim other benefits from their design, including reduced cycle times compared to previously known designs. Still other crystallizer designs continue to be introduced in the literature, and may be considered for use in one or more of the melt crystallization stages schematically depicted in FIG. 2, see, e.g., the hydraulic wash column described by Verdoes and Bassett, "High Purity Products by Crystallization", Specialty Chemicals, vol. 29, no. 7, pp. 32-35 (2009) and Funakoshi et al., "Influences of reflux ratio on separation and purification of acrylic acid by inclined column crystallizer", Journal of Crystal Growth 237-239, pp. 2251-2256 (2002).

Falling film crystallizations are generally carried out in a multitube exchanger, with each tube being fed continuously at its top with a liquid stream (a melt) of acrylic acid from which propionic acid is to be removed, which liquid falls as a film along the internal wall of the tube, is received at the tube bottom and recirculated at the top of the tube for as long as necessary in a closed loop for the crystallization of the desired amount of acrylic acid on the internal tube wall. Concurrently, a heat exchange fluid, typically being ethylene glycol/water or methanol/water, flows along the external wall of the tube and provides the cooling or heating necessary for the operation of each stage of a crystallization cycle, with recycling from the tube bottom to the tube top for the duration of the crystallization cycle.

Each crystallization stage itself proceeds in three phases or stages: crystallization, sweating and melting. In the crystallization stage, the temperature of the heat exchange fluid is lowered along a negative temperature gradient, starting from a temperature slightly above the crystallization temperature of the acrylic acid in the melt, typically 14 degrees Celsius. Crystals form on the surface of the inner tube wall. When approximately 30 to 80 percent of the acrylic acid circulated has crystallized, the remaining liquid fraction—the mother liquor—is drained away and removed. In sweating, the temperature of the heat exchange fluid is raised along a positive temperature gradient in order to remove, by melting, impurities (in this case, principally propionic acid) trapped in the form of inclusions in the layer of acrylic acid crystals being formed; these inclusions occur increasingly as the layer is built up, through contact with the recirculating impure acrylic acid which is increasingly concentrated in the propionic acid as acrylic acid is crystallized out. In the melting stage, the temperature of the heat exchange liquid is rapidly increased above the melting point of acrylic acid (14 degrees Celsius) but not to an extent whereby polymerization occurs (for example, not higher than 35 to 40 degrees Celsius), and the crystalline layer melts and is collected. Typically the crystalline layer from a first crystallizer is supplied to a second crystallizer as the melt, so that through sequenced operation higher purities can be achieved as illustrated in certain examples below.

In a particular embodiment illustrated schematically in FIG. 2 which utilizes both chromatography and melt crystallization as just described, a second flash vessel 74 flashes off lighter components in stream 76, while the remainder 78, consisting of more than 98 percent pure acrylic acid but still containing propionic acid in excess of a preferred upper limit of 3000 ppm by weight, is then conveyed to a first melt crystallization stage 80.

The mother liquor 82 from stage 80 enters a second melt crystallization stage 84, while the crystallizate 86 from the second melt crystallization stage 84 is combined with the crystallizate 88 from the first melt crystallization stage 80, and the combined crystallizates 86 and 88 are fed to a third melt crystallization stage 90. The mother liquor 92 from the second stage 84 is combined with the propionic acid-containing bottoms stream 94 from the second distillation column in a typical two-column sequence just described, and this combination is used as the feed to a simulated moving bed chromatographic system 96. An acrylic acid product 98 from the preferred simulated moving bed chromatographic system in step 40 is then fed to the third melt crystallization stage 90 alongside crystallizates 86 and 88, while the raffinate stream 100 from the simulated moving bed chromatographic system 96 is predominantly comprised of excess propionic acid contained in the crude acrylic acid product 50.

In one embodiment, in an optional further step residual acrylic acid remaining with the propionic acid in raffinate stream 100 is hydrogenated in a reactor 102 with hydrogen 104 to produce additional propionic acid and thereby provide a higher purity propionic acid co-product 106. In certain embodiments, the hydrogenation can be carried out in the manner described in the above-referenced U.S. Pat. No. 8,440,859 to Dubois. It should be noted, however, that whereas Dubois contemplates that the material being hydrogenated will contain from 50 to 90 percent by weight of acrylic acid, the acrylic acid content in our raffinate 100 will be very much less than 50 percent by weight. Accordingly, accomplishing Dubois's desired propionic acid purity of at least 85 percent by weight, preferably at least 95 percent by weight, and more preferably at least 99% by weight, should ultimately be considerably easier in our process wherein, for example, the raffinate 100 contains 7.9 percent by weight of residual acrylic acid (Example 28) rather than being mostly comprised of acrylic acid as in Dubois.

As related in U.S. Pat. No. 8,440,859 to Dubois, the hydrogenation can be carried out in the liquid or gas phase with a source of molecular hydrogen. Known methods of carrying out the hydrogenation referenced by Dubois include FR 2219927, Chemicky Prumsyl 37, pp. 651-653 (1987) and Electroanalytical Chemistry (1975), pp. 75-80. Particularly described are: a homogeneous liquid phase process using a ruthenium-phosphine complex and methanol as a solvent, carried out at approximately 60 degrees Celsius and at a pressure of approximately 3 MPa; heterogeneous gas-phase catalysis over a copper/zinc on aluminum oxide catalyst in a fixed bed, at a temperature between 250 degrees and 350 degrees Celsius and a pressure of between 0.1 MPa and 0.6 MPa (from 1 to 6 atmospheres); and heterogeneous catalysis over a palladium catalyst applied in the form of a liquid palladium salt solution adsorbed on a porous support, such as silicic acid or an active charcoal, the salt being subsequently reduced to form metallic platinum, at a temperature of from 20 to 80 degrees Celsius and a hydrogen pressure of from 0.1 MPa to 1.0 MPa (1 to 10 atmospheres).

In another embodiment, by means of a less-preferred alternative further step excess propionic acid in the raffinate 100 is oxidatively dehydrogenated to provide additional acrylic acid, for example, by a catalyst and method as described in EP 2039674 B1 to Han et al, wherein a mixed metal oxide catalyst of the formula $A_aM_bN_cX_dZ_eO_f$ is used, where A is "at least one element selected from the group consisting of Mo and W; M is at least one element selected from the group consisting of V and Ce; N is at least one element selected from the group consisting of Te, Sb and Se; X is at least one element consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and O is oxygen in oxide form and wherein, when a=1, b=0.01 to 1.0, c=0.01 to 1.0, d=0.01 to 1.0, e=0 to 0.1, and f is dependent on the oxidation state of the other elements". Preferred catalysts were "$Mo_aV_mTe_nNb_xO_o$ and $W_aV_mTe_nNb_xO_o$ wherein a, m, n, x and o [sic-f?] are as previously defined". Alternatively, a MoFeCoO catalyst and method as described in the JP 2000053611 reference mentioned by Han et al. may be used. In another alternative embodiment, a catalyst and method as described in JP 07-330658 to Keiko (assigned to Daicel Chemical Industries Ltd) wherein propionic acid or its corresponding ester are oxidatively dehydrogenated using a catalyst of the formula $P_aMo_bV_cA_dCe_eB_fO_g$, where A is one or more of copper, arsenic, antimony, silicon, tungsten, chromium, silver and magnesium, B is one or more of potassium, rubidium, cesium and thallium, (a) is from 0.5 to 3, (c) is from 0.1 to 3, (d) is from 0 to 3, (e) is from 0.01 to 3, (f) is from 0.01 to 2 and (g) is as required when (b) is 12. In another alternative embodiment, a catalyst and process may be used as described in McEntee et al, "Selective Catalytic Oxidative-Dehydrogenation of Carboxylic Acids-Acrylate and Crotonate Formation at the Au/TiO$_2$ Interface", J. Am. Chem. Soc. Vol. 136, pp. 5116-5120 (2014), wherein a gold on titania catalyst was employed. In still another alternative embodiment, a catalyst and method may be used as described in U.S. Pat. No. 3,855,279 to Watkins, wherein (as specifically shown in Example 9) propionic acid may be oxidatively dehydrogenated to acrylic acid using a catalyst comprised of the calcined residue of the mixed phosphates of iron and lead in the presence of oxygen and at temperatures in the range of from 250 degrees Celsius to 600 degrees Celsius. This additional acrylic acid can likewise be processed by chromatography, by crystallization or by a combination of chromatography and crystallization as illustrated herein.

A glacial acrylic acid product stream 108, containing preferably less than 3000 ppm by weight of propionic acid and more preferably less than 1000 ppm by weight of propionic acid, is produced from the third melt crystallization stage 90, while the mother liquor 110 from the third melt crystallization stage 90 is recycled to the beginning of the crystallizer sequence, to the first melt crystallization stage 80.

This invention is further illustrated by the following non-limiting examples:

EXAMPLES

Example 1

A series of pulse tests were performed on an acrylic acid/propionic acid mixture using a DIAION AMP-03 amphoteric ion exchange resin. The standard test procedure involved charging 100 ml of the resin to a 1.5 cm diameter glass column as a slurry in water at room temperature. The resin was then washed with 500 ml of water. Water was drained to the top of the resin, then a 6 ml pulse of feed was charged to the resin column. The liquid was again drained to the top of the resin, and 2 ml of water added. Again, the liquid was drained to the top of the resin, then 10 ml of water was added to the head space. Water was flowed through the resin at 3 ml/minute while collecting a 6 ml fraction at intervals. The 6 ml fractions were then analyzed.

Following the above procedure, it was found as shown in FIG. 3 that both acetic and propionic acids can be separated from acrylic acid by means of SMB chromatography using an amphoteric ion exchange resin such as the DIAION AMP-03 amphoteric ion exchange resin under isocratic conditions.

Examples 2-4

The pulse test performed in Example 1 shows that the SMB chromatographic separation of acrylic acid from propionic acid is technically possible. However, the water requirements would most likely be quite significant due to the late elution and slight tailing of the acrylic acid peak. One potential solution would be to use either an organic solvent or a mixture of water and organic solvent to decrease the elution requirements. Following the above procedure, different levels of methanol and acetone were evaluated in combination with water in Examples 2-4 to see if the retention and peak shape of the acrylic acid could be improved.

The use of 5% acetone in water (Ex. 2 and FIG. 4) showed that the retention time of the acrylic acid peak could be decreased by 0.5 bed volumes and the tail decreased by about 1 bed volume, indicating that elution requirements could in fact be reduced compared to the isocratic separation in an SMB chromatographic separation.

Methanol as a co-solvent at 15% in the elution in a pulse test (Example 3 and FIG. 5) also decreased elution requirements and improved the peak shape of all of the acid peaks. Increasing the relative concentration of methanol to 50% (Example 4 and FIG. 6) significantly decreased the elution time of the acrylic acid but the peak overlap of the acrylic and propionic acid peaks increased to the point where the SMB chromatographic separation would most likely not be successful.

Examples 5-9

Figure 7:
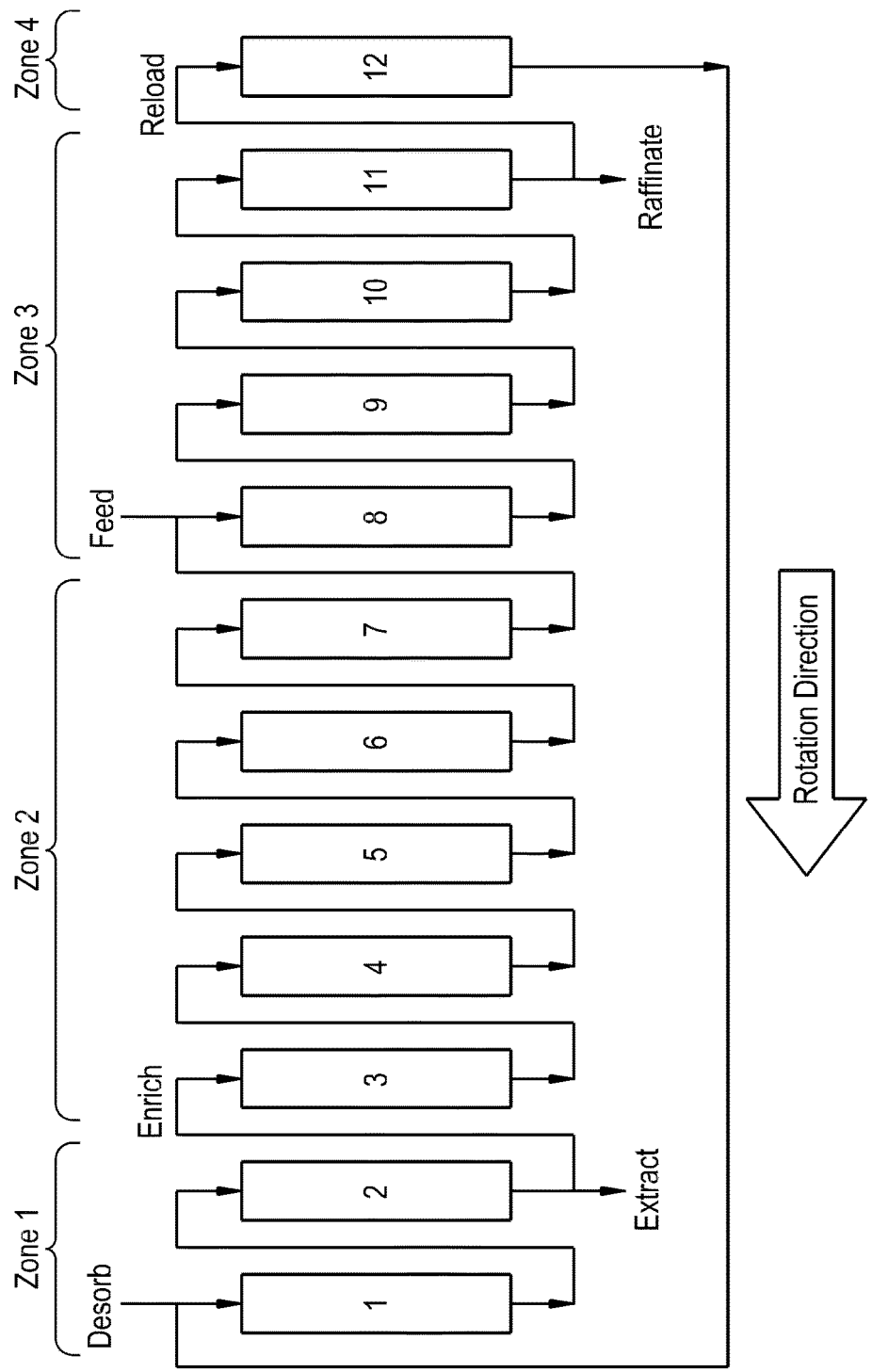
FIG. 7 schematically depicts a 12-column simulated moving bed chromatographic apparatus used in certain of the examples below based on the initial pulse testing.

The pulse tests reported in Examples 1-4 confirm that SMB chromatography may be used for the separation of acrylic acid from both acetic and propionic acid using both isocratic conditions and with mixed solvents as the eluent, though because of the difference in the boiling points of acetic acid and acrylic acid, a distillative separation may be preferred as to the acetic acid byproduct. To further evaluate the performance of the various eluents in an SMB chromatographic arrangement, a 12-column carousel SMB chromatography unit was arranged in a 2-5-4-1 column arrangement employing the DIAION AMP-03 amphoteric ion exchange resin (see FIG. 7). Four individual pumps were operated independently for the desorb, enrich, feed and reload streams.

Table 1 shows a series of experiments run using the 12-column arrangement and isocratic conditions, with all flows reported being in grams/minute:

TABLE 1

| | Experiment | | | | |
|---|---|---|---|---|---|
| | 1 | 2 | 3 | 4 | 5 |
| Step Time (min) | 12 | 12 | 12 | 12 | 12 |
| Feed | 4.71 | 4.76 | 4.38 | 4.38 | 4.17 |
| Enrich | 18.35 | 18.89 | 21.04 | 16.18 | 15.5 |
| Elution | 25.26 | 28.1 | 23.33 | 20.32 | 20.67 |
| Extract | 20.92 | 22.2 | 17.29 | 20.14 | 21.17 |
| Raffinate | 9 | 10.48 | 11.04 | 4.56 | 4.17 |
| Reload | 14 | 13 | 15 | 16 | 16 |
| Zone I flow | 39.26 | 41.1 | 38.33 | 36.32 | 36.67 |
| Zone II flow | 18.34 | 18.9 | 21.04 | 16.18 | 15.5 |
| Zone III flow | 23.05 | 23.66 | 25.42 | 20.56 | 19.67 |
| Zone IV flow | 14 | 13 | 15 | 16 | 16 |
| % Acrylic | 95.6 | 99.6 | 57 | 88.4 | 94.9 |
| % Acrylic | 99.3 | 99.2 | >99.9 | 99.3 | 99.1 |
| Acrylic Conc. | 28.7 | 25.5 | 21.4 | 30.3 | 31.4 |
| Propionic Conc. (g/L) | 0.2 | 0.2 | 0 | 0.2 | 0.3 |

As the data in Table 1 show, a 99+ percent pure acrylic acid product was realized relative to propionic acid at a recovery of more than 95 percent. The feed contained from 100-150 g/liter of acrylic acid combined with from 7-15 g/liter of propionic acid.

Examples 10-18

Table 2 shows a series of experimental runs using the 12-column arrangement but with 10% acetone in an acetone/water combination eluent:

TABLE 2

| Experiment | 1 | 2 | 3 | 4 | 5 | 6 | 7 | 8 | 9 |
|---|---|---|---|---|---|---|---|---|---|
| Step Time | 12 | 1 | 1 | 1 | 1 | 1 | 12 | 1 | 12 |
| Feed | 4.79 | 4.83 | 4.75 | 4.86 | 4.76 | 5 | 5 | 5 | 5 |
| Enrich | 13.96 | 15 | 14.58 | 15.56 | 15.71 | 15.76 | 15.42 | 15.13 | 14.58 |
| Elution | 15.07 | 14.33 | 13.5 | 14.14 | 14.6 | 14.68 | 14.6 | 14.71 | 14.69 |
| Extract | 16.11 | 15.33 | 14.92 | 14.58 | 14.88 | 14.92 | 15.19 | 15.58 | 16.11 |
| Raffinate | 3.54 | 3.75 | 3.42 | 4.42 | 4.36 | 4.45 | 4.09 | 4 | 3.72 |
| Reload | 15 | 1 | 16 | 16 | 1 | 16 | 1 | 1 | 16 |
| Zone I flow | 30.07 | 30.33 | 29.5 | 30.14 | 30.6 | 30.68 | 30.6 | 30.71 | 30.69 |
| Zone II flow | 13.96 | 1.5 | 14.58 | 15.56 | 15.72 | 15.76 | 15.41 | 15.13 | 14.58 |
| Zone III flow | 18.75 | 19.83 | 19.33 | 20.42 | 20.48 | 20.76 | 20.41 | 20.13 | 19.58 |
| Zone IV flow | 15 | 1 | 1 | 1 | 1 | 1 | 1 | 1 | 16 |
| % Acrylic | 98.38 | 96.7 | 99.05 | 98.2 | 97.1 | 50.33 | 58.5 | 74.4 | 90.1 |
| % Acrylic | 92.7 | 95.9 | 99.3 | 99.4 | 99.7 | 99.6 | 99.6 | 99.3 | 98.7 |
| Acrylic Conc. (g/L) | 41.9 | 35 | 27.1 | 31.4 | 37.5 | 25 | 28 | 30 | 39 |
| Propionic Conc (g/L) | 3.3 | 1.5 | 0.2 | 0.2 | 0.1 | 0.1 | 0.1 | 0.2 | 0.5 |

As expected from the pulse tests, when changing the elution solvent to include 10% acetone the desired yield and purities were achieved with a significant decrease in elution requirements from Examples 5-9, from 5:1 elution:feed for the isocratic separation to 3:1 for the mixed acetone/water eluent. This results in increased extract concentrations and decreased evaporation. Solvent recovery costs may offset these benefits to an extent.

Examples 19-27

Table 3 shows a series of experimental runs conducted with 25% methanol as a co-solvent:

TABLE 3

| Experiment | 1 | 2 | 3 | 4 | 5 | 6 | 7 | 8 | 9 |
|---|---|---|---|---|---|---|---|---|---|
| Step Time (min) | 12 | 12 | 12 | 12 | 12 | 12 | 12 | 12 | 12 |
| Feed | 5 | 5 | 4.42 | 4.54 | 4.58 | 4.38 | 4.49 | 4.5 | 4.39 |
| Enrich | 13.23 | 14.91 | 15.25 | 12.69 | 13.44 | 13.75 | 15.19 | 14.94 | 15.68 |
| Elution | 15.15 | 14.93 | 15 | 14.83 | 14.21 | 14.1 | 15.09 | 14.61 | 14.91 |
| Extract | 17.92 | 16.02 | 15.75 | 18.15 | 16.77 | 16.35 | 15.9 | 15.67 | 15.23 |
| Raffinate | 1.92 | 3.63 | 3.42 | 0.67 | 1.6 | 1.81 | 3.36 | 3.11 | 4 |
| Reload | 16 | 16 | 16 | 16 | 16 | 16 | 16 | 16 | 16 |
| Zone I flow | 31.15 | 30.93 | 31 | 30.83 | 30.21 | 30.1 | 31.09 | 30.61 | 30.91 |
| Zone II flow | 13.23 | 14.91 | 15.25 | 12.69 | 13.44 | 13.75 | 15.19 | 14.94 | 15.68 |
| Zone III flow | 18.23 | 19.91 | 19.67 | 17.22 | 18.02 | 18.13 | 19.68 | 19.44 | 20.07 |
| Zone IV flow | 16 | 16 | 16 | 16 | 16 | 16 | 16 | 16 | 16 |
| % Acrylic Recovery | 99.2 | 67.1 | 63.6 | 98.7 | 96.1 | 93.4 | 98.4 | 86.4 | 94.87 |
| % Acrylic Purity | 98.7 | 99.3 | 100 | 96.4 | 98.7 | 98.4 | 97.4 | 99.5 | 99.3 |
| Acrylic conc (g/l) | 37.3 | 30 | 28 | 37 | 31 | 37 | 37.5 | 38 | 41.3 |
| Propionic conc (g/l) | 0.5 | 0.2 | 0 | 1.4 | 0.4 | 0.6 | 1 | 0.2 | 0.3 |

Again, the desired yield and purities were able to be achieved, with a significant decrease in elution requirements compared to isocratic operation.

Example 28

A melt crystallization and chromatography sequence as shown schematically in FIG. 2 was modeled using commercially available ASPENPLUS (Version 8.2) process modeling software from Aspen Technology, Inc., Burlington, Mass., following a series of melt crystallization experiments that were conducted on various combinations of acrylic acid and propionic acid in order to construct an equilibrium phase diagram and determine the eutectic composition between acrylic acid and propionic acid, and further based on the chromatographic testing summarized above. Results of the modeling are shown below in Table 4, for an incoming remainder 78 of the overhead stream 72 from a second distillation column 70 and a propionic acid-containing bottoms stream 94 from the second distillation column 70, in a preceding process for making biobased acrylic acid generally according to U.S. Pat. No. 4,786,756 to Paparizos et al.

Examples 29-32

A series of batch trials were conducted on the extraction of lactic acid from a fermentation broth that had been produced using a process according to U.S. 2012/0214214 to Hara et al. and then filtered by ultrafiltration.

A solvent combination of Alamine® 304-1 water-insoluble tri-octyl/dodecyl amine (BASF SE, Ludwigshafen, Germany) and n-octanol in a 25:75 ratio was intimately mixed with the ultrafiltered fermentation broth for each batch trial. After allowing phase separation over a period ranging from thirty minutes to sixty minutes for a quantitative separation, the organic solvent phase containing extracted lactic acid and the fermentation broth remainder were analyzed by ion exclusion HPLC to determine how much of the lactic had been extracted from the fermentation broth. The organic solvent was then regenerated by back extraction with a 26 Baume (29.4 weight percent) aqueous ammonium hydroxide solution, and after a further phase separation, the ammonium lactate solution formed was then analyzed by ion exclusion HPLC for lactic acid and by use of an ammonia ion specific electrode for ammonia.

The regenerated solvent was then used for extraction of a further quantity of ultrafiltered fermentation broth, and the steps of the preceding batch trial repeated, until four batches of ultrafiltered fermentation broth had been processed.

TABLE 4

| Flow# | 78 | 88 | 108 | 82 | 110 | 86 | 92 | 94 | 98 | 106 |
|---|---|---|---|---|---|---|---|---|---|---|
| Mass flow, kg/hr | 100 | 105.6 | 114.7 | 54.39 | 60.03 | 35.28 | 19.10 | 36.96 | 33.79 | 22.27 |
| Vol. flow, l/min | 1.563 | 1.65 | 1.791 | 0.851 | 0.939 | 0.551 | 0.3 | 0.59 | 0.528 | 0.359 |
| Density Kg/m$^3$ | 1066.6 | 1066.8 | 1067.1 | 1065.2 | 1066.1 | 1066.6 | 1062.8 | 1044.9 | 1066.9 | 1034.7 |
| Mass fraction | | | | | | | | | | |
| Acrylic | 0.984 | 0.991 | 0.997 | 0.961 | 0.977 | 0.987 | 0.914 | 0.478 | 0.988 | 0.079 |
| Propionic | 0.016 | 0.009 | 0.003 | 0.039 | 0.023 | 0.013 | 0.086 | 0.522 | 0.012 | 0.921 |

Results of the four batch trials were as follows:

Trial 1:

| | |
|---|---|
| Volume of ultrafiltered broth | 500 ml |
| Lactic concentration in broth | 71.6 g/kg |
| Volume of solvent mix | 820 ml |
| Raffinate recovered | 448 ml |
| Lactic concentration in raffinate | 10 g/kg |
| pH of raffinate | not determined |
| Ammonium hydroxide added | 28 ml |
| Ammonium lactate recovered | 72 ml |
| Pct. lactic extracted | 87.2% |
| Lactic concentration in ammonium lactate | 34.8% |
| Ammonia concentration in lactate | 8.32% |
| Ammonium lactate solution concentration | 41.37% (calc) |

Trial 2

| | |
|---|---|
| Volume of ultrafiltered broth | 300 ml |
| Lactic concentration in broth | 70.7 g/kg |
| Volume of solvent mix | 800 ml |
| Raffinate recovered | 276 ml |
| Lactic concentration in raffinate | 16.4 g/kg |
| pH of raffinate | 4.93 |
| Ammonium hydroxide added | 18 ml |
| Ammonium lactate recovered | 52 ml |
| Pct. lactic extracted | 80% |
| Lactic concentration in ammonium lactate | 31.7% |
| Ammonia concentration in lactate | 8.42% |
| Ammonium lactate solution concentration | 37.7% (calc) |

Trial 3

| | |
|---|---|
| Volume of ultrafiltered broth | 300 ml |
| Lactic concentration in broth | 70.7 g/kg |
| Volume of solvent mix | 800 ml |
| Raffinate recovered | 280 ml |
| Lactic concentration in raffinate | 12.64 g/kg |
| pH of raffinate | 4.77 |
| Ammonium hydroxide added | 17.5 ml |
| Ammonium lactate recovered | 50 ml |
| Pct. lactic extracted | 83.4% |
| Lactic concentration in ammonium lactate | 33.4% |
| Ammonia concentration in lactate | 9.39% |
| Ammonium lactate solution concentration | 39.7% (calc) |

Trial 4

| | |
|---|---|
| Volume of ultrafiltered broth | 300 ml |
| Lactic concentration in broth | 70.9 g/kg |
| Volume of solvent mix | 810 ml |
| Raffinate recovered | 277 ml |
| Lactic concentration in raffinate | 16.5 g/kg |
| pH of raffinate | 4.83 |
| Ammonium hydroxide added | 17.5 ml |
| Ammonium lactate recovered | 48 ml |
| Pct. lactic extracted | 78.6% |
| Lactic concentration in ammonium lactate | 33.8% |
| Ammonia concentration in lactate | 8.9% |
| Ammonium lactate solution concentration | 40.2% (calc) |

Example 33

For this Example and the next, a LiquiCel® MiniModule® membrane contactor equipped with hydrophobic X50 polypropylene tubular membranes (Membrana GmbH, Wuppertal, Germany) was employed.

In a first trial, 1.25 liters of ultrafiltered fermentation broth was extracted across the X50 tubular membranes in the membrane contactor into 2.5 liters of a 25:75 mixture of Alamine® 336 water-insoluble tri-n-dodecyl amine (BASF SE, Ludwighafen, Germany) and 2,6-dimethyl-4-heptanol. The solvent mixture was circulated on the shell side of the tubular membranes, while the fermentation broth was circulated through the lumen side. The trial was carried out over 5.67 hours. The feed lactic concentration was 66.8 g/kg, and the ending broth concentration was 14.5 g/kg. About 2.3 liters of the lactic acid-bearing solvent mixture was recovered at the end of the trial, with a small aqueous layer being noted but not separated prior to back extraction of the lactic acid-bearing solvent mixture with 69 ml of 26 Baume aqueous ammonia solution. The ammonia solution and lactic acid-bearing solvent mixture were mixed well over 64 minutes, then allowed to phase separate. 172 mL of aqueous ammonium lactate solution was recovered. Analysis showed a lactic acid concentration of 339.6 g/kg and 89 g/kg of ammonia in the ammonium lactate solution. The calculated ammonium lactate concentration was 40.4 weight percent.

Example 34

In a second trial, 1.14 liters of ultrafiltered fermentation broth was extracted across the X50 tubular membranes in the membrane contactor into 2.5 liters of a 25:75 mixture of Alamine® 336 water-insoluble tri-n-dodecyl amine (BASF SE, Ludwighafen, Germany) and 2,6-dimethyl-4-heptanol. The solvent mixture was circulated on the shell side of the tubular membranes, while the fermentation broth was circulated through the lumen side. The trial was carried out over 5.1 hours. The feed lactic concentration was 64.7 g/kg, and the ending broth concentration was 11.7 g/kg. About 1 liter of the extracted fermentation broth was recovered at the close of the trial, while about 2.5 liters of the lactic acid-bearing solvent mixture was recovered. The lactic acid-bearing solvent mixture was then back extracted with 65 ml of 26 Baume aqueous ammonia solution. The ammonia solution and lactic acid-bearing solvent mixture were mixed well over 45 minutes, then allowed to phase separate. 162 mL of aqueous ammonium lactate solution was recovered. Analysis showed a lactic acid concentration of 367 g/kg and 100 g/kg of ammonia in the ammonium lactate solution. The calculated ammonium lactate concentration was 43.6 weight percent, and about 84 percent of the lactic acid in the ultrafiltered fermentation broth was recovered in the ammonium lactate product.

What is claimed is:
1. A process for making acrylic acid from dextrose, comprising:
 a. fermenting dextrose in the presence of a biological catalyst to produce a fermentation broth containing lactic acid;
 b. removing solids from the fermentation broth to produce a clarified fermentation broth;
 c. removing lactic acid from the clarified fermentation broth by extraction into an organic solvent;
 d. separating the lactic acid-loaded organic solvent from the fermentation broth remainder after lactic acid has been removed therefrom;
 e. recycling at least a portion of the fermentation broth remainder to the fermentation step;
 f. reacting lactic acid in the lactic acid-loaded solvent with ammonia to provide a crude dehydration feed comprising ammonium lactate;
 g. separating ammonium lactate from organic solvent in the crude dehydration feed to provide a dehydration feed;

h. carrying out a vapor phase dehydration of ammonium lactate in the dehydration feed to produce a crude acrylic acid product;

i. purifying the crude acrylic acid product to provide a purified acrylic acid product, by a process including a first distillation to remove acetaldehyde and ammonia overhead and provide a bottoms stream comprised predominantly of acrylic acid and propionic acid, and a second distillation of the bottoms stream from the first distillation to provide a second distillation overhead stream enriched in acrylic acid and a second distillation bottoms stream enriched in propionic acid; and, j. further purifying the acrylic acid in the second distillation overhead stream by contacting with an the amphoteric ion exchange resin to separate and elute propionic acid into a raffinate or both melt crystallization and by contacting with an the amphoteric ion exchange resin to separate and elute propionic acid into a raffinate.

2. A process according to claim 1, wherein the purified acrylic acid product of step j) contains less than 3000 ppm by weight of propionic acid.

3. A process according to claim 2, wherein the purified acrylic acid product of step j) contains less than 1000 ppm by weight of propionic acid.

4. A process according to claim 1, wherein the separation of lactic acid from the clarified fermentation broth comprises the use of one or more hydrophilic nanofiltration membranes.

5. A process according to claim 1, wherein the fermentation of dextrose comprises the use of an acid-resistant transformant of *Schizosaccharomyces pombe*, a recombinant strain of *Schizosaccharomyces pombe* or an acid-tolerant yeast strain comprising a genome that includes an exogenous lactate dehydrogenase gene.

6. A process according to claim 5, wherein the further purification involves both melt crystallization and adsorption onto an amphoteric ion exchange resin.

7. A process according to claim 1, wherein the contacting is accomplished in a series of columns and the eluent passes through the columns as a simulated moving bed.

8. A process according to claim 1 wherein the amphoteric ion exchange resin has a quaternary ammonium group and a carboxy group incorporated on a cross-linked polystyrene frame.

9. A process according to either of claim 1 wherein an eluent of water or of water in combination with an organic solvent is used in step j).

10. A process according to claim 9, wherein the organic solvent is methanol or acetone.

* * * * *